(12) United States Patent
Zhang et al.

(10) Patent No.: US 10,889,575 B2
(45) Date of Patent: Jan. 12, 2021

(54) 4,4-DIPHENYLPIPERIDINE COMPOUNDS OR PHARMACEUTICALLY ACCEPTABLE SALTS THEREOF, PHARMACEUTICAL COMPOSITIONS AND USES THEREOF

(71) Applicant: Academy of Military Medical Sciences, Beijing (CN)

(72) Inventors: Cheng Zhang, Beijing (CN); Haoshan Wang, Beijing (CN); Guoxing Dong, Beijing (CN); Ning Wu, Beijing (CN); Shuzhuo Zhang, Beijing (CN); Xiaomei Zhuang, Beijing (CN); Chong Pang, Beijing (CN); Juan Wang, Beijing (CN); Rifang Yang, Beijing (CN); Jianquan Zheng, Beijing (CN); Jin Li, Beijing (CN); Liuhong Yun, Beijing (CN)

(73) Assignee: Academy of Military Medical Sciences, Beijing (CN)

( * ) Notice: Subject to any disclaimer, the term of this patent is extended or adjusted under 35 U.S.C. 154(b) by 0 days.

(21) Appl. No.: 16/477,655

(22) PCT Filed: Jan. 12, 2018

(86) PCT No.: PCT/CN2018/072426
§ 371 (c)(1),
(2) Date: Jul. 12, 2019

(87) PCT Pub. No.: WO2018/130207
PCT Pub. Date: Jul. 19, 2018

(65) Prior Publication Data
US 2019/0359604 A1    Nov. 28, 2019

(30) Foreign Application Priority Data

Jan. 13, 2017 (CN) .......................... 2017 1 0023076

(51) Int. Cl.
| | | |
|---|---|---|
| C07D 409/06 | (2006.01) | |
| C07D 221/00 | (2006.01) | |
| C07D 241/04 | (2006.01) | |
| C07D 413/10 | (2006.01) | |

(52) U.S. Cl.
CPC ......... C07D 409/06 (2013.01); C07D 221/00 (2013.01); C07D 241/04 (2013.01); C07D 413/10 (2013.01)

(58) Field of Classification Search
CPC .. C07D 409/06; C07D 221/00; C07D 241/04; C07D 413/10
See application file for complete search history.

(56) References Cited

U.S. PATENT DOCUMENTS

| | | | |
|---|---|---|---|
| 4,016,280 A | | 4/1977 | Menge et al. |
| 5,036,075 A | * | 7/1991 | Comte ................. C07D 513/06 514/293 |
| 6,566,376 B1 | | 5/2003 | Baxter et al. |
| 6,593,344 B1 | * | 7/2003 | Biedermann ........... A61P 35/02 514/318 |

(Continued)

FOREIGN PATENT DOCUMENTS

| | | |
|---|---|---|
| CA | 2 605 985 A | 11/2006 |
| CN | 1361775 A | 7/2002 |

(Continued)

OTHER PUBLICATIONS

International Search Report (ISR) for PCT/CN2018/072426; I.A. fd: Jan. 12, 2018, dated Apr. 27, 2018, State Intellectual Property Office of the P.R. China, Beijing, China.

(Continued)

*Primary Examiner* — Timothy R Rozof
(74) *Attorney, Agent, or Firm* — Sterne, Kessler, Goldstein & Fox P.L.L.C.

(57) ABSTRACT

The invention belongs to the field of medicine and chemical industry and relates to a 4,4-diphenylpiperidine compound or a pharmaceutically acceptable salt thereof, a pharmaceutical composition comprising the same and uses thereof. In particular, the invention relates to a compound of Formula I or a pharmaceutically acceptable salt thereof, and to a pharmaceutical composition comprising the compound or a pharmaceutically acceptable salt thereof. In the present invention, the compound or pharmaceutically acceptable salt thereof and the pharmaceutical composition have significant activity in blocking an N-type calcium channel, and have good pharmacokinetic properties, can effectively relieve pain, and have a potential as a new medicament for prevention or treatment of pain, stroke, cerebral ischemia, alcohol addiction, alcoholism, kidney disease, addictive disorder caused by analgesic or tolerance disorder caused by analgesic.

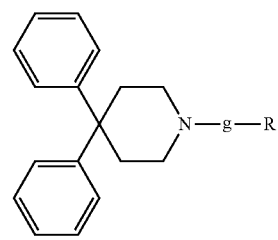

I

12 Claims, 2 Drawing Sheets

(56) References Cited

U.S. PATENT DOCUMENTS

| | | | |
|---|---|---|---|
| 7,381,719 B2 * | 6/2008 | Blanco-Pillado | C07D 217/02 514/227.5 |
| 2002/0019389 A1 * | 2/2002 | Kim | C07D 403/12 514/213.01 |
| 2004/0204404 A1 | 10/2004 | Zelle et al. | |
| 2009/0192169 A1 | 7/2009 | Egle et al. | |
| 2009/0215742 A1 * | 8/2009 | Funk | C07D 403/10 514/211.1 |
| 2016/0016941 A1 * | 1/2016 | Canney | A61P 25/28 514/253.11 |

FOREIGN PATENT DOCUMENTS

| | | | |
|---|---|---|---|
| CN | 101454292 A | | 6/2009 |
| CN | 102239146 A | | 11/2011 |
| DE | 1966199 | * | 11/1971 |
| WO | WO 01/95856 A2 | | 12/2001 |
| WO | WO 2008/031227 A1 | | 3/2008 |
| WO | WO 2008/043183 A1 | | 4/2008 |
| WO | WO 2010/039947 A1 | | 4/2010 |
| WO | WO 2016/183150 A1 | | 11/2016 |

OTHER PUBLICATIONS

International Preliminary Report on Patentability (IPRP) (Chapter II of the Patent Cooperation Treaty; PCT Article 36 and Rule 70) for PCT/CN2018/072426; I.A. fd: Jan. 12, 2018; dated Jul. 16, 2019, by The International Bureau of WIPO, Geneva, Switzerland.

Klumpp, DA et al., "Dicationic intermediates involving protonated amides: dual modes of reactivity including the acylation of arenes," Org Lett. May 27, 2004;6(11):1789-92.

STN International, Columbus, Ohio, (Jun. 13, 2014), 692717-79-6/CAS RN; 1-Butanone, 4-(4,4-diphenyl-1-piperidinyl)-1-phenyl.

STN International, Columbus, Ohio, (Oct. 24, 2004), 768332-29-2/CAS RN; Piperidine, 1-[(3,4-dihydro-8-methoxy-2H-1-benzopyran-2-yl)methyl] -4,4-diphenyl.

Notice of the First Examination Opinion for CN Appl. No. 201710023076, dated Dec. 20, 2019 From the State Intellectual Property Office, Beijing, CN.

STN International, Columbus, OH search prepared Dec. 2, 2019, CAS Registration No: 1609830-84-3, 2-pyrrolidinone, 1-[3-(4,4-diphenyl-1-piperidinyl)-3-oxopropyl]—(CA index name) entry dated Jun. 6, 2014.

* cited by examiner

4,4-DIPHENYLPIPERIDINE COMPOUNDS OR PHARMACEUTICALLY ACCEPTABLE SALTS THEREOF, PHARMACEUTICAL COMPOSITIONS AND USES THEREOF

TECHNICAL FIELD

The invention belongs to the field of medicinal chemical industry and relates to a 4,4-diphenylpiperidine compound or a pharmaceutically acceptable salt thereof, a pharmaceutical composition comprising the compound or pharmaceutically acceptable salt thereof, and uses thereof.

BACKGROUND ART

N-type calcium ion channel belongs to a subtype of voltage-dependent calcium ion channel (VDCC). It is composed of α1β subunit and featured with high voltage activation and rapid inactivation. It is mainly distributed in nerve tissue, can be blocked by w-conotoxin GVIA (wCgTx), and has been identified as a novel drug target with clinical relevance.

Blockers for N-type calcium ion channel have a good application prospect in treatment of stroke and cerebral ischemia, analgesia, especially inhibition of neuropathic pain, reduction of alcohol cravings and treatment of alcoholism[1] as well as renal protection[2,3,4].

The results of researches show that N-type calcium ion channel is an important part of pain production and pain conduction, and the blockers for N-type calcium ion channel are not easy to generate addiction because they directly act on N-type calcium ion channel and do not involve second messenger or G protein. At present, the highly selective blocker for N-type calcium ion channel, ω-conotoxin MVIIA (Piralt®), was approved by the FDA of the USA in December 2004, and its clinical practice shows that N-type calcium ion channel blockers have been proven to be a novel target for the treatment of pain and have good application prospects.

Current researches indicate that blockade of N-type calcium ion channels is associated with treatment of kidney diseases:

On the one hand, the blockade of N-type calcium ion channel reduces the release of norepinephrine and renin from sympathetic nerve endings, reduces the resistance of afferent glomerular arterioles and efferent glomerular arterioles, and reduces the pressure of glomerulus[2]. In the diabetic state, the rennin-angiotensin system of renal is inappropriately activated, the activity of angiotensin-converting enzyme (ACE) is increased, the expression of angiotensin II (Ang II) is increased, which directly involve in progressive damage of the kidney; it not only causes high pressure in the glomerulus by affecting the hemodynamics in the whole body and kidney, but also closely relates to the protein kinase C (PKC) theory, oxidative stress (OS) theory, cytokine theory and genetic molecular theory in the pathogenesis of diabetic nephropathy (DN). There are sympathetic nerves and parasympathetic nerves distributing in the kidney, and most of the intrarenal sympathetic nerves are vasomotor, which cause renal vasoconstriction. The N-type calcium ion channel is located at the sympathetic nerve endings, and after the excitation of sympathetic nerves, the influx of calcium ions in the N-type calcium ion channel and the release of norepinephrine cause the contraction of afferent and efferent glomerular arterioles and stimulate the release of renin from juxtaglomerular cells. Moreover, among the many factors of diabetic nephropathy development, renal hemodynamics, especially glomerular hyperperfusion pressure, plays a key role in renal function damage. In 2005, Tomoyuki[3] et al. reported that in the rat model of hypertensive nephropathy, L/N-type calcium ion channel blocker Cilnidipine significantly reduced the levels of plasma renin and norepinephrine and the pressures of afferent and efferent glomerular arterioles, and reduced microalbuminuria. By inhibiting the N-type calcium ion channel to reduce microalbuminuria, the kidney may be protected.

On the other hand, the blockade of N-type calcium ion channel results in the increase of sensitivity to insulin and the decrease of insulin resistance[4]. The mechanism of insulin resistance (IR) causing diabetic nephropathy may be to stimulate the accumulation of extracellular matrix, increase various inflammatory cytokines, increase sodium retention, and cause damage to kidney. Due to the increase in blood insulin resulted by IR, hyperinsulinemia may excite the hypothalamic sympathetic nerve center, and also affect renal hemodynamics, directly acting on the glomerular artery, dilating afferent glomerular arterioles, aggravating glomerular hyperfiltration and hyperperfusion state, promoting glomerular sclerosis by indirect mechanisms such as hypertension, hyperlipidemia and hyperuricemia, and hyperinsulinemia aggravates the occurrence of glomerular hypertrophy by stimulating cytokines such as insulin-like growth factors. This is confirmed with early pathological manifestations of type 2 diabetic nephropathy, i.e., slight widening of the mesangial matrix and slight thickening of the glomerular basement membrane (GBM). Some experts suggest that IR is not only the root cause of diabetes, but also the basis for the formation of kidney disease in diabetic patients. In 1999, Ishikawa et al.[4] observed that the N-type calcium ion channel blocker Cilnidipine reduced insulin resistance in a hypertensive nephropathy model, whereas the L-type calcium ion channel blocker Amlodipine did not have this function. These results further confirm that N-type calcium ion channel may be a potential new therapeutic target for the treatment of kidney diseases.

At present, several series of small molecule compounds have been developed as N-type calcium ion channel blockers[5]. Among them, small molecule compounds, "4-piperidinyl anilines", disclosed in WO99/43658 exhibit significant analgesic activity as an orally selective N-type calcium ion channel blocker; Teodori et al.[6], Knutsen et al.[7], Yamamoto et al.[8,9], Tyagarajan et al.[10] have also made some progresses; the small molecule blocker for N-type calcium ion channel, NMED-160, has entered the phase II clinical study, and the related compounds have also been studied and showed good results[11,12].

However, the currently available blockers for N-type calcium ion channel have the following defects: on the one hand, these compounds have insufficient biological activity and channel selectivity; on the other hand, the pharmacokinetic properties of these compounds are poor, resulting in that clinically complex and difficult routes such as lateral ventricle administration may have to be used to produce sufficient pharmacological activity. Therefore, there is still a need to develop a novel N-type calcium ion channel blocker.

CONTENTS OF THE INVENTION

The inventors have obtained a group of 4,4-diphenylpiperidine compounds or pharmaceutically acceptable salts thereof by researches and creative works. The inventors have found that these compounds or pharmaceutically acceptable salts thereof exhibit remarkable activity of blocking N-type calcium ion channel, have good pharmacokinetic properties, can effectively prevent or alleviate pain, and are potential new drugs or pharmaceutically active ingredients for prevention and/or treatment of pain (especially neuropathic pain), stroke, cerebral ischemia, alcohol addiction, alcoholism, kidney disease, addictive disorder caused by analgesic drug, or tolerant disorder caused by analgesic drug.

A first aspect of the invention relates to a compound of Formula I or a pharmaceutically acceptable salt thereof:

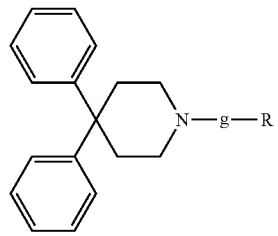

I wherein:
g is selected from the group consisting of $C_{1-8}$ alkylidene, substituted $C_{1-8}$ alkylidene, carbonyl and $C_{1-8}$ alkylideneacyl;
R is selected from the group consisting of $C_{5-20}$ aryl, substituted $C_{5-20}$ aryl, $C_{4-20}$ heterocyclyl and substituted $C_{4-20}$ heterocyclyl;
the substituted $C_{1-8}$ alkylidene, substituted $C_{5-20}$ aryl and substituted $C_{4-20}$ heterocyclyl each are independently substituted with one or more substituents, the substituent is selected from the group consisting of halogen, $C_{1-8}$ alkyl, $C_{1-8}$ alkoxy, $C_{3-8}$ cycloalkyl, cyano, nitro, mercapto, methylthio, ethylthio, trifluoromethyl, amino, amido, mono-$C_{1-8}$ alkylamino, di-$C_{1-8}$ alkylamino, $C_{1-8}$ alkylsulfonyl, hydroxy, aryloxy, heteroaryloxy and heterocyclyloxy.

In the present invention, the pharmaceutically acceptable salts of the Formula I compound comprise inorganic or organic acid salts thereof, including but not limited to, hydrochloride, hydrobromide, hydroiodide, nitrate, sulfate, hydrogen sulfate, phosphate, hydrogen phosphate, acetate, glycolate, propionate, butyrate, oxalate, adipate, alginate, lactate, citrate, tartrate, succinate, maleate, fumarate, picrate, aspartate, gluconate, benzoate, methanesulfonate, ethanesulfonate, besylate, tosylate, pamoate, pyruvate, glycolate, malonate, trifluoroacetate, malate, salicylate, p-aminosalicylate, pamoate and ascorbate, etc.; for example, a hydrochloride of the compound of Formula I.

Any one of the compounds in the first aspect of the invention maybe a prodrug or in a form which may release the active ingredient after metabolic alteration in vivo. The selection and preparation of a suitable prodrug derivative are well known to those skilled in the art.

In certain embodiments of the first aspect of the invention, g is selected from the group consisting of $C_{1-8}$ alkylidene, carbonyl and $C_{1-8}$ alkylideneacyl; R is selected the group consisting from $C_{5-20}$ aryl, substituted $C_{5-20}$ aryl and $C_{4-20}$ heterocyclyl.

In certain embodiments of the first aspect of the present invention, the substituted $C_{5-20}$ aryl is substituted with one or more substituents, the substituent is selected from the group consisting of $C_{1-8}$ alkyl, $C_{1-8}$ alkoxy, $C_{3-8}$ cycloalkyl, mercapto, methylthio, ethylthio, amino, mono-$C_{1-8}$ alkylamino, alkylamino and hydroxy.

In certain embodiments of the first aspect of the invention, the halogen is fluorine, chlorine, bromine or iodine.

In certain embodiments of the first aspect of the invention, g is selected from the group consisting of $C_{1-8}$ alkylidene, carbonyl and $C_{1-8}$ alkylideneacyl; R is selected from the group consisting of $C_{6-12}$ aryl, substituted $C_{6-12}$ aryl and $C_{4-12}$ aromatic heterocyclyl.

In certain embodiments of the first aspect of the invention, the substituted $C_{6-12}$ aryl is substituted with one or more substituents, the substituent is selected from the group consisting of $C_{1-8}$ alkoxy, methylthio, ethylthio, amino, mono-$C_{1-8}$ alkylamino and di-$C_{1-8}$ alkylamino.

In certain embodiments of the first aspect of the invention, the $C_{4-12}$ aromatic heterocyclyl is $C_{4-5}$ aromatic heterocyclyl or $C_{6-12}$ benzoheterocyclyl.

In certain embodiments of the first aspect of the invention, g is selected from the group consisting of methylene, carbonyl, methyleneacyl, ethylideneacyl, 1,3-propylideneacyl, 1,2-propylideneacyl, 1,4-butylideneacyl, 1,3-butylideneacyl, 1,2-butylideneacyl; R is selected from the group consisting of phenyl, substituted phenyl, thienyl and benzoxazolinonyl (for example, 2-benzoxazolinonyl).

In certain embodiments of the first aspect of the invention, the substituted phenyl is substituted with one or more substituents, the substituent is selected from the group consisting of methoxy and dimethylamino.

In certain embodiments of the first aspect of the invention, the compound or pharmaceutically acceptable salt thereof is selected from the group consisting of the following Compounds (1) to (6) and pharmaceutically acceptable salts thereof:

(1) 6-(3-(4,4-diphenylpiperidinyl)-propionyl)benzoxazolin-2-one;
(2) 6-(3-(4,4-diphenylpiperidinyl)-acetyl)benzoxazolin-2-one;
(3) 1-(4-dimethylaminobenzyl)-4,4-diphenylpiperidine;
(4) 1-(3,4,5-trimethoxybenzyl)-4,4-diphenylpiperidine;
(5) 1-(2-methylthienyl)-4,4-diphenylpiperidine;
(6) 4,4-diphenyl-1-benzylpiperidine.

The names and structural formulas of the above Compounds (1) to (6) are shown in Table 1 below.

TABLE 1

Names and structural formulas of Compounds (1) to (6)

| Cpd. No. | Name | Structural Formula |
|---|---|---|
| (1) | 6-(3-(4,4-diphenylpiperidinyl)-propionyl) benzoxazolin-2-one | |

TABLE 1-continued

Names and structural formulas of Compounds (1) to (6)

| Cpd. No. | Name | Structural Formula |
|---|---|---|
| (2) | 6-(3-(4,4-diphenylpiperidinyl)-acetyl)benzoxazolin-2-one | |
| (3) | 1-(4-dimethylaminobenzyl)-4,4-diphenyl-piperidine | |
| (4) | 1-(3,4,5-trimethoxybenzyl)-4,4-diphenyl-piperidine | |
| (5) | 1-(2-methylthienyl)-4,4-diphenylpiperidine | |
| (6) | 4,4-diphenyl-1-benzylpiperidine | |

A second aspect of the invention relates to a process for preparing any one of the compounds or a pharmaceutically acceptable salt thereof in the first aspect of the invention.

The Formula I compound of the present invention can be prepared by a synthetic route as shown below, and in addition, by referring to the detailed description in the examples of the invention. If necessary, the compound can also be reacted with an acid and be converted into its pharmaceutically acceptable salts.

First, N-benzyl-4-piperidone as a raw material is reacted with benzene as a raw material and a reactive solvent to obtain 4,4-diphenyl-1-benzylpiperidine (Formula II) at room temperature in the presence of trifluoromethanesulfonic acid; then, 4,4-diphenyl-1-benzylpiperidine (Formula II) is reacted with ethyl chloroformate and then is hydrolyzed with alkaline to produce 4,4-diphenylpiperidine (Formula IV); the 4,4-diphenylpiperidine (Formula IV) in anhydrous acetone is stirred together with a commercially available halide or aldehyde for 2 to 24 hours at room temperature in the presence of an alkaline such as triethylamine for halogenation or reductive amination to obtain the target compound of Formula I.

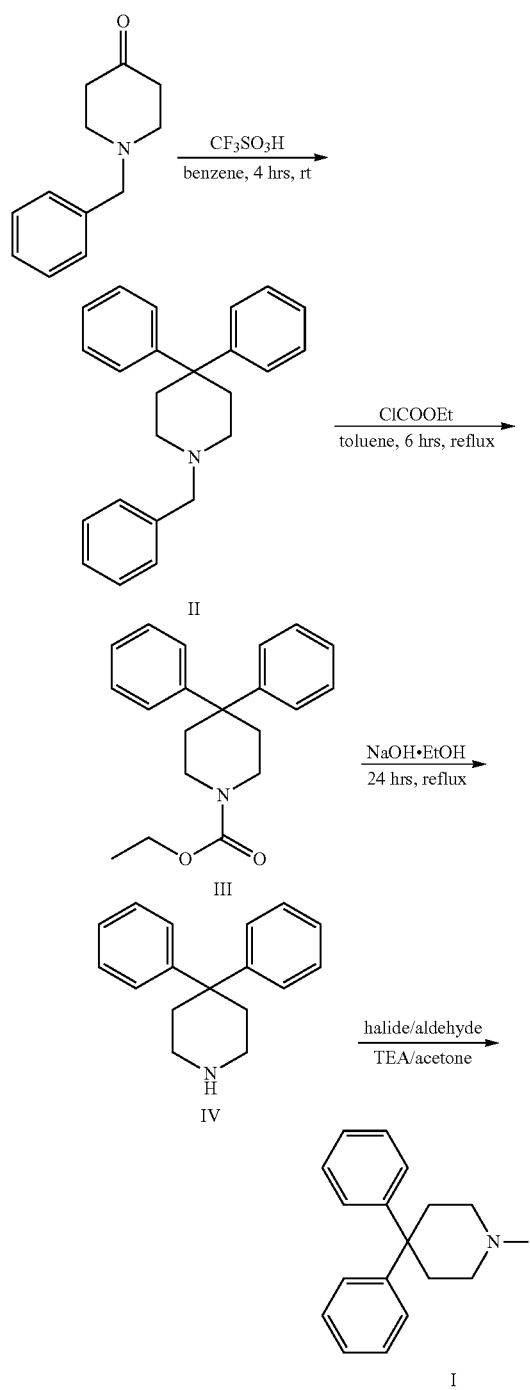

compounds or a pharmaceutically acceptable salt thereof according in the first aspect of the present invention, comprises the steps of:

(1) N-benzyl-4-piperidone is reacted with benzene in the presence of trifluoromethanesulfonic acid to form a compound of Formula II,

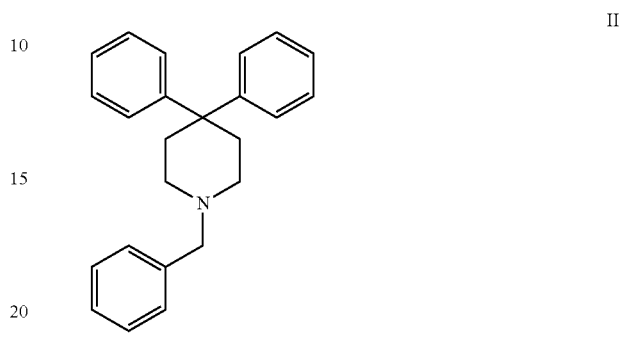

(2) the compound of Formula II is reacted with ethyl chloroformate to form a compound of Formula III,

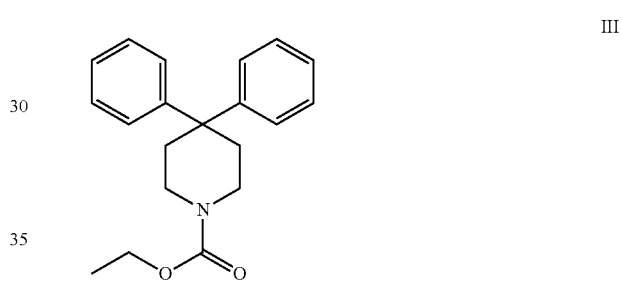

(3) the compound of Formula III is hydrolyzed under alkaline condition to form a compound of Formula IV,

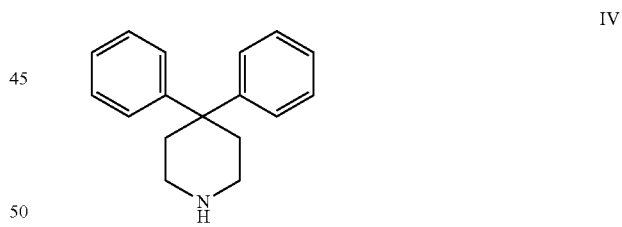

(4) the compound of Formula IV is reacted with a halide or an aldehyde to form a compound of Formula I,

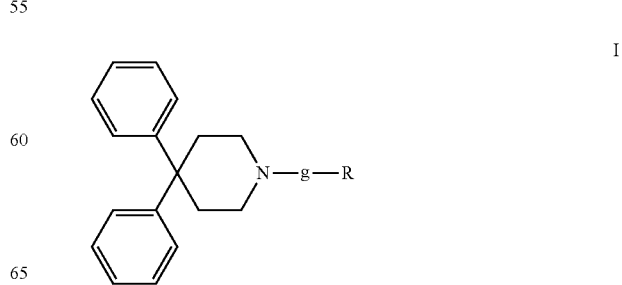

In certain embodiments of the second aspect of the present invention, the process for preparing any one of the the definition of R or g in the above Formula I is described as any one of the compounds or a pharmaceutically acceptable salt thereof in the first aspect of the invention.

A third aspect of the invention relates to a pharmaceutical composition, which comprising any one of the compounds or a pharmaceutically acceptable salt thereof according to the first aspect of the invention; optionally, the pharmaceutical composition further comprises a pharmaceutically acceptable carrier and/or excipient.

The compound of the invention may be administered by itself or in the form of a pharmaceutical composition. In the pharmaceutical composition of the invention, the compound may be admixed with one or more pharmaceutically acceptable carriers, excipients or diluents. The pharmaceutical composition of the present invention is usually prepared by a conventional manner using one or more physiologically acceptable carriers and/or excipients which facilitate the processing of the active compound into a preparation suitable for medical uses. A suitable preparation depends on the selected route of administration and can be prepared according to common knowledge well known in the art.

The pharmaceutical carriers or excipients that can be used in the pharmaceutical composition of the invention include, but are not limited to, ion exchangers, alumina, aluminum stearate, lecithin, serum proteins such as human serum albumin, buffer substances such as phosphates, glycerin, sorbic acid, potassium sorbate, mixtures of partial glycerides of saturated plant fatty acids, water, salts or electrolytes, for example, protamine sulfate, disodium hydrogen phosphate, potassium hydrogen phosphate, sodium chloride, zinc salts, colloidal silica, magnesium trisilicate, polyvinylpyrrolidone, cellulose materials, polyethylene glycol, sodium carboxymethylcellulose, polyacrylates, beeswax, polyethylene-polyoxypropylene block polymer, lanolin.

In the present invention, the Formula I compound or pharmaceutically acceptable salt thereof, or the pharmaceutical composition comprising the Formula I compound or pharmaceutically acceptable salt thereof, may be administered via a enteral or parenteral route such as oral route, muscle route, subcutaneous route, nasal route, oral mucosa route, skin route, peritoneum route or rectum route, etc. The drug form may be a tablet, capsule, drop pill, aerosol, pill, powder, solution, suspension, emulsion, granule, liposome, transdermal agent, buccal tablet, suppository, lyophilized powder, etc. It may also be prepared as a sustained release preparation, a controlled release preparation, and various microparticle delivery systems.

A fourth aspect of the invention relates to a method of blocking or inhibiting a N-type calcium ion channel in vivo or in vitro, comprising a step of: administering to a subject in need thereof an effective amount of any one of the compounds or a pharmaceutically acceptable salt thereof according to the first aspect of the invention, or administering to a subject in need thereof an effective amount of the pharmaceutical composition of the third aspect of the invention.

A fifth aspect of the invention relates to a use of any one of the compounds or a pharmaceutically acceptable salt thereof according to the first aspect of the invention or the pharmaceutical composition of the third aspect of the invention in the manufacture of a N-type calcium ion channel blocker or inhibitor.

A sixth aspect of the invention relates to a use of any one of the compounds or a pharmaceutically acceptable salt thereof according to the first aspect of the invention or the pharmaceutical composition according to the third aspect of the invention in manufacture of a medicament for prevention or treatment of a pain, a stroke, a cerebral ischemia, an alcohol addiction, an alcoholism, a renal disease, an addictive disorder caused by an analgesic drug or a tolerance disorder caused by an analgesic drug; for example, the pain is a postoperative pain, a migraine, a visceral pain or a neuropathic pain; for example, the renal disease is an acute renal failure, a chronic renal failure, or a renal insufficiency.

A seventh aspect of the invention relates to a method for prevention or treatment of a pain, a stroke, a cerebral ischemia, an alcohol addiction, an alcoholism, a renal disease, an addictive disorder caused by an analgesic drug or a tolerable disorder caused by an analgesic drug, comprising the step of: administering to a subject in need thereof an effective amount of any one of the compounds or a pharmaceutically acceptable salt thereof according to the first aspect of the invention, or the pharmaceutical composition according to the third aspect of the invention; for example, the pain is a postoperative pain, a migraine, a visceral pain or a neuropathic pain; for example, the renal disease is an acute renal failure, a chronic renal failure or a renal insufficiency.

The compound of the present invention or a pharmaceutically acceptable salt thereof can be administered alone or in combination with other compounds or a pharmaceutically acceptable salt thereof of the present invention, and/or in combination with other known therapeutic agents.

The specific dosage and administering method for different patients of the compounds or a pharmaceutically acceptable salt thereof of the present invention or the pharmaceutical composition of the present invention depend on many factors, including age, weight, sex, natural health status and nutritional status of the patients, activity intensity of compound, administration time, metabolism rate, severity of disease, and subjective judgment of physicians.

A unit dosage form generally contains 0.1 wt % to 99 wt % active substance, more typically 5 wt % to 75 wt % active substance. For example, the unit dosage form may contain 1 mg to 1 g, 10 mg to 500 mg, 50 mg to 400 mg, or 100 mg to 200 mg of the compound.

The eighth aspect of the invention relates to any one of the compounds or a pharmaceutically acceptable salt thereof according to the first aspect of the invention, or the pharmaceutical composition according to the third aspect of the invention, for use in blocking or inhibiting a N-type calcium ion channel.

The ninth aspect of the invention relates to any one of the compounds or a pharmaceutically acceptable salt thereof according to the first aspect of the invention, or the pharmaceutical composition according to the third aspect of the invention, for use in prevention or treatment of a pain, a stroke, a cerebral ischemia, an alcohol addiction, an alcoholism, a renal disease, an addictive disorder caused by an analgesic drug or a tolerable disorder caused by an analgesic drug; for example, the pain is a postoperative pain, a migraine, a visceral pain or a neuropathic pain; for example, the renal disease is an acute renal failure, a chronic renal failure or a renal insufficiency.

In the present invention, unless otherwise specified:

The term "halogen" refers to a Group VIIA element, including fluorine (F), chlorine (Cl), bromine (Br), iodine (I) and astatine (At).

The term "$C_{1-8}$ alkyl" refers to a straight or branched alkyl having 1 to 8 carbon atoms, for example, a linear or branched alkyl having 1 to 6 carbon atoms, for example, a linear or branched alkyl having 1 to 4 carbon atoms, such as methyl, ethyl, propyl, isopropyl, butyl, isobutyl, sec-butyl, tert-butyl, pentyl, 2-ethyl-butyl, hexyl, heptyl and octyl.

The term "$C_{1-8}$ alkylidene" refers to a straight or branched alkyl which has 1 to 8 carbon atoms and from which two hydrogen atoms are formally eliminated, for example, $C_{1-6}$ alkylidene, $C_{1-4}$ alkylidene, methylene, 1,2-ethylidene, ethylidene, isopropylidene, 1,3-propylidene, etc.

The term "carbonyl" refers to a divalent group of carbon and oxygen atoms linked by a double bond.

The term "$C_{1-8}$ alkylideneacyl" refers to the rest group of $C_{1-8}$ alkyl fatty acid after removing a hydroxyl and also eliminating a hydrogen atom, such as, $C_{2-8}$ alkylideneacyl, $C_{2-6}$ alkylideneacyl, $C_{1-6}$ alkylideneacyl, methyleneacyl, ethylideneacyl, 1,3-propylideneacyl, 1,2-propylideneacyl, 1,4-butylideneacyl, 1,3-butylideneacyl, 1,2-butylideneacyl, and the like.

The term "$C_{1-8}$ alkoxy" refers to "$C_{1-8}$ alkyl-O—", in which $C_{1-8}$ alkyl is defined as above.

The term "$C_{3-8}$ cycloalkyl" refers to a cyclic alkyl having 3 to 8 carbon atoms, for example, $C_{3-6}$ cycloalkyl, $C_{3-5}$ cycloalkyl, and the examples of $C_{3-8}$ cycloalkyl include cyclopropyl, cyclobutyl, cyclopentyl, cyclohexyl, cycloheptyl, cyclooctyl, and the like.

The term "$C_{5-20}$ aryl" refers to an aromatic ring (including fused rings) which has 5 to 20 carbon atoms, and from which one hydrogen is formally eliminated, for example, $C_{6-20}$ aryl, $C_{6-18}$ aryl, $C_{6-12}$ aryl. Examples of aryl specifically include cyclopentadienyl, phenyl, naphthyl, anthracyl, fluorenyl, and the like.

The term "aryloxy" refers to "aryl-O—", in which aryl is defined as above for the $C_{5-20}$ aryl.

The term "$C_{4-20}$ heterocyclyl" refers to a heterocyclic group having 4 to 20 atoms (in which 1 to 3 atoms are selected from heteroatoms of oxygen, nitrogen and sulfur), and is classified into aliphatic heterocyclyl and aromatic heterocyclyl. Examples of heterocyclyl include benzoheterocyclyl, tetrahydrofuranyl, pyrrolidinyl, piperidinyl, morpholinyl, thiazolidinyl, thiazolinethionyl, thiothiazolinyl, benzothiazolyl, thiophenyl, thiadiazolyl, benzoxazoline-2-ketone group, and the like.

The term "heterocyclyloxy" refers to "heterocyclyl-O—", in which heterocyclyl is defined as above for the $C_{4-20}$ heterocyclyl.

The term "heteroaryl" refers to an aromatic heterocyclyl, in which 1 to 3 atoms are selected from heteroatoms of oxygen, nitrogen and sulfur. Examples of heteroaryl include $C_{5-20}$ heteroaryl, $C_{5-12}$ heteroaryl, pyrrolyl, pyridyl, imidazolyl, furyl, pyranyl, thienyl, pyrimidinyl, pyrazinyl, pyridazinyl, indolyl, quinolyl, pyridopyridyl, carbazolyl, and the like.

The term "heteroaryloxy" refers to "heteroaryl-O—", in which heteroaryl is defined as above for the $C_{5-20}$ heteroaryl.

The term "polysubstitution" refers to a substitution with a plurality of substituents, examples thereof include disubstitution, trisubstitution, tetrasubstitution, and the like.

The term "administration" includes all means of directly or indirectly releasing a compound/pharmaceutical composition to the intended site of action.

The term "amido" refers to a group formed from a carboxylic acid by replacing the hydroxyl therein with an amino (or amine) group and formally eliminating one hydrogen atom.

The term "$C_{1-8}$ alkylsulfonyl" refers to a sulfonyl group substituted with a $C_{1-8}$ alkyl, wherein the $C_{1-8}$ alkyl is defined as above for the $C_{1-8}$ alkyl.

The term "mercapto" refers to the abbreviation of sulfhydryl (—SH), also known as "thiol", which is a monovalent atomic group composed of two elements i.e. hydrogen and sulfur. Mercapto is one of the essential groups in certain enzyme proteins.

The term "$C_{1-8}$ alkylamino" refers to a group resulted from the substitution of hydrogen atoms in the amino group with $C_{1-8}$ alkyl, wherein the $C_{1-8}$ alkyl is defined as above for the $C_{1-8}$ alkyl. "Mono-$C_{1-8}$ alkylamino" means that one hydrogen atom in the amino group is substituted with a $C_{1-8}$ alkyl. "Di-$C_{1-8}$ alkylamino" means that two hydrogen atoms in the amino group are substituted with $C_{1-8}$ alkyl.

The term "$C_{4-12}$ aromatic heterocyclyl" refers to a group having 4 to 12 carbon atoms, which has a relatively stable ring system, wherein the ring including heteroatoms is planar with 4n+2 π electrons in a ring-closed conjugated system, such as, benzoxazolinonyl, and pyridyl, thienyl, furyl in $C_{4-5}$ aromatic heterocyclyl groups, and the like.

The term "$C_{6-12}$ benzoheterocyclyl" refers to a group having 6 to 12 carbon atoms, formed by fusing of benzene ring and monoheterocyclic ring, for example, benzoxazolinonyl.

The term "blockade" refers to completely (totally) blocking or partially blocking, for example a blockade with a blocking rate of more than 10%, more than 20%, more than 30%, more than 40%, more than 50%, more than 60%, more than 70%, more than 80%, or 100%. "Blocker" refers to a medicament used to achieve this blocking.

The beneficial effects obtained by the invention:

1. The compound or a pharmaceutically acceptable salt thereof and a pharmaceutical composition comprising the same according to the present invention have a significant and specific effect of blocking or inhibiting on N-type calcium ion channel.

2. The compound or a pharmaceutically acceptable salt thereof and a pharmaceutical composition comprising the same according to the present invention have good pharmacokinetic properties and can effectively relieve pain.

3. The compound or a pharmaceutically acceptable salt thereof and a pharmaceutical composition comprising the same according to the present invention can prevent or treat a postoperative pain, a migraine, a visceral pain, a neuropathic pain, a stroke, a cerebral ischemia, an alcohol addiction, an alcoholism, an acute renal failure, a chronic renal failure, a renal insufficiency, an addictive disorder caused by an analgesic drug or a tolerable disorder caused by an analgesic drug.

BRIEF DESCRIPTION OF THE DRAWINGS

In order to make the content of the present invention more easily understood, the present invention will be further described in detail in combination with the specific embodiments and the accompanying drawings of the invention below, in which.

Example 1

Figure 1:
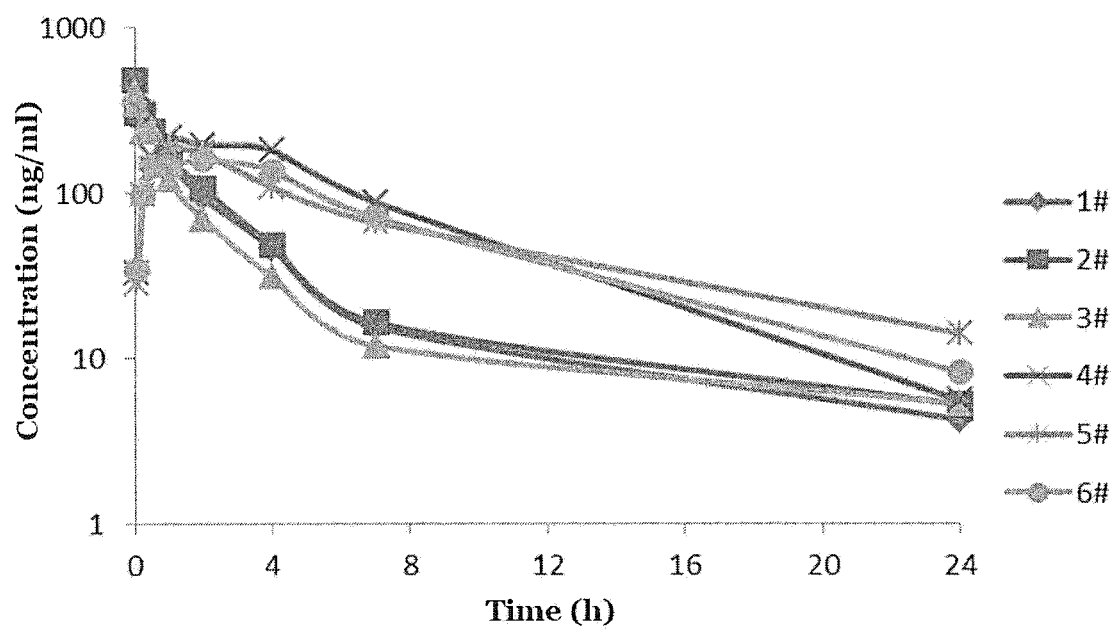
FIG. 1 shows the concentrations of Compound (1) in plasmas of 6 rats in Test Example 4 of the present invention.

Synthesis of 6-(3-(4,4-diphenylpiperidinyl)-propionyl) benzoxazolin-2-one (Compound (1))

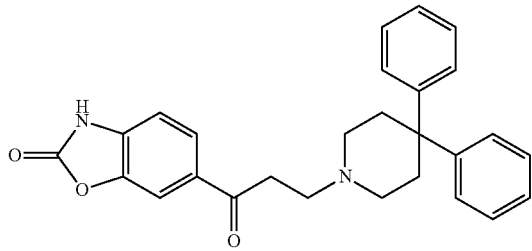 [SMILES: O=C(CCN1CCC(c2ccccc2)(c2ccccc2)CC1)c1ccc2[nH]c(=O)oc2c1]

1.89 g (0.01 mol) of N-benzyl-4-piperidone was weighed and dissolved in 20 mL of dry benzene, added with 20 mL of trifluoromethanesulfonic acid under stirring, and stirred for 4 hours at room temperature. The reaction liquid was poured into ice water, added with 40% sodium hydroxide aqueous solution to adjust pH to 10-12, extracted for 3 times each with 30 mL of dichloromethane. The extracts were combined and washed first with 30 mL of saturated sodium chloride solution and second with 30 mL of water, then added with an appropriate amount of anhydrous sodium sulfate and stood overnight for drying, filtered to remove the drying agent, and evaporated under reduced pressure to remove solvent and to give 3.24 g of white solid (4,4-diphenyl-1-benzylpiperidine, Compound (6)), yield 99%.

3.24 g of the 4,4-diphenyl-1-benzylpiperidine (Compound (6)) prepared above was dissolved in 100 mL of toluene, added with 20 mL of ethyl chloroformate, heated and refluxed for 8 hours reaction. After evaporating the solvent under reduced pressure, 100 mL of distilled water and 8 mL of 40% sodium hydroxide aqueous solution were added to the residue, and the reaction was performed under heating and reflux for 24 hours. The solvent was evaporated under reduced pressure, and 100 mL of distilled water was added thereto, and extraction was performed for 3 time each with 40 mL of dichloromethane. The extracts were combined and washed first with 30 mL of saturated sodium chloride solution and second with 30 mL of water, added with an appropriate amount of anhydrous sodium sulfate and stood overnight for drying, filtered to remove the drying agent, and evaporated under reduced pressure to remove solvent and to give 1.81 g of white solid, which was 4,4-diphenylpiperidine, m.p.: 148° C.-150° C., yield: 76.0%. $^1$H-NMR (CDCl$_3$, ppm) δ: 7.30-7.34 (m, 4H), 7.20-7.23 (m, 6H), 3.21 (t, 4H, J=5.32 Hz), 2.68 (t, 4H, J=5.32 Hz).

0.47 g (0.002 mol) of the 4,4-diphenylpiperidine and 0.45 g (0.002 mol) of 6-(3-chloropropionyl)benzoxolin-2-one prepared above were dissolved in 30 mL of acetone, added with 0.22 g (0.002 mol) of triethylamine, and stirred at room temperature for 24 hours. After suction filtration, the resulted solid was washed with diethyl ether and water, and dried to obtain 0.52 g of white solid (Compound (1)), m.p.: 236° C. (decomposition), yield: 61.0%. $^1$H-NMR (DMSO-d$_6$, ppm) δ: 7.79-7.81 (m, 2H), 7.10-7.34 (m, 11H), 3.12 (t, 2H, J=7.00 Hz), 2.41-2.58 (m, 10H). MS [M+H]$^+$: 427.3.

Example 2

Synthesis of 6-(3-(4,4-diphenylpiperidinyl)-acetyl) benzoxazolin-2-one (Compound (2))

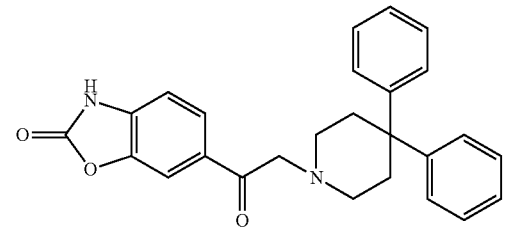 [SMILES: O=C(CN1CCC(c2ccccc2)(c2ccccc2)CC1)c1ccc2[nH]c(=O)oc2c1]

0.47 g (0.002 mol) of 4,4-diphenylpiperidine (prepared by referring to the method of Example 1) and 0.45 g (0.002 mol) of 6-(2-chloroacetyl)benzoxazolin-2-one were taken and dissolved in 30 mL of acetone, added with 0.22 g (0.002 mol) of triethylamine, and stirred at room temperature for 24 hours. After suction filtration, the resulted solid was washed with diethyl ether and water, and dried to obtain 0.44 g of white solid (Compound (2)), yield: 52.0%. $^1$H-NMR (DMSO-d$_6$, ppm) δ: 7.79-7.81 (m, 2H), 7.10-7.34 (m, 11H), 3.76 (s, 2H), 2.40-2.53 (m, 8H). MS[M+H]$^+$: 425.2.

Example 3

Synthesis of 1-(4-dimethylaminobenzyl)-4,4-diphenylpiperidine (Compound (3))

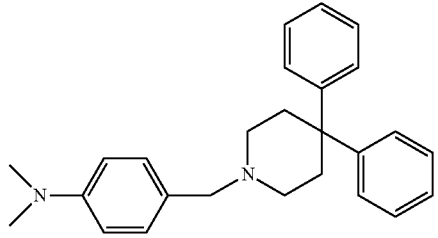 [SMILES: CN(C)c1ccc(CN2CCC(c3ccccc3)(c3ccccc3)CC2)cc1]

0.47 g (0.002 mol) of 4,4-diphenylpiperidine (prepared by referring to the method of Example 1) and 0.30 g (0.002 mol) of 4-dimethylaminobenzaldehyde were weighed and dissolved in 25 mL of dry dichloromethane, stirred at room temperature for 1 hour; 0.53 g (0.0025 mol) of sodium triacetoxyborohydride was added thereto under the cooling of ice water bath, and further stirred for 30 minutes in ice water bath, and then warmed to room temperature and continuously stirred for 8 hours. The reaction mixture was added with 20 mL of dichloromethane, and washed with saturated sodium hydrogencarbonate aqueous solution, saturated sodium chloride aqueous solution and water 30 mL each. The dichloromethane layer was separated, added with an appropriate amount of anhydrous sodium sulfate and stood overnight for drying, filtered to remove drying agent, evaporated under reduced pressure to remove solvent, and separated by silica column to obtain 0.49 g of white solid (Compound (3)), m.p.: 128° C.-130° C., yield: 66.1%. $^1$H-NMR (CDCl$_3$, ppm) δ: 7.12-7.29 (m, 12H), 6.68 (d, 2H, J=8.68 Hz), 3.34 (s, 2H), 2.48-2.51 (brs, 8H). MS [M+H]$^+$: 371.0.

Example 4

Synthesis of 1-(3,4,5-trimethoxybenzyl)-4,4-diphenylpiperidine hydrochloride (Compound (4) hydrochloride)

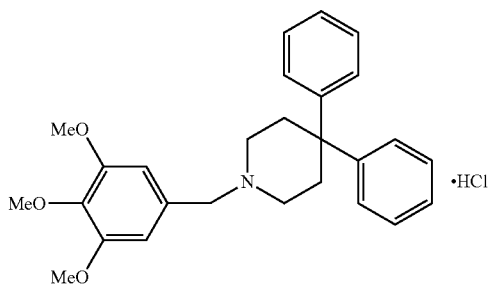 [SMILES: COc1cc(CN2CCC(c3ccccc3)(c3ccccc3)CC2)cc(OC)c1OC ; Cl]

0.47 g (0.002 mol) of 4,4-diphenylpiperidine (prepared by referring to the method of Example 1) and 0.19 g (0.002 mol) of 3,4,5-trimethoxybenzaldehyde were weighed, and the synthesis was performed by referring to the method of Example 3 to give a pale yellow oily substance (Compound (4)), the salifying was performed with diethyl ether solution of hydrogen chloride to obtain 0.46 g of white solid (Compound (4) hydrochloride), m.p.: 235° C.-237° C., yield: 55.1%. $^1$H-NMR (CDCl$_3$, ppm) δ: 12.51 (br, 1H), 7.44-7.48 (t, 2H, J=7.56 Hz), 7.03-7.46 (m, 10H), 3.91 (s, 6H), 3.85 (s, 3H), 3.45 (t, 2H), 2.13 (t, 2H), 2.71 (t, 4H). MS [M+H]$^+$: 418.6.

Example 5

Synthesis of 1-(2-methylthienyl)-4,4-diphenylpiperidine (Compound (5))

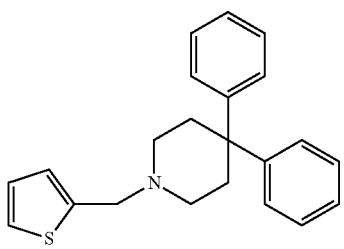 [SMILES: c1ccc(C2(c3ccccc3)CCN(Cc3cccs3)CC2)cc1]

0.47 g (0.002 mol) of 4,4-diphenylpiperidine (prepared by referring to the method of Example 1) and 0.22 g (0.002 mol) of 2-thiophenaldehyde were weighed, and the synthesis was performed by referring to the method of Example 3 to give 0.56 g of white solid (Compound (5)), yield: 84.1%. $^1$H-NMR (DMSO-d$_6$, ppm) δ: 6.88-7.41 (m, 11H), 3.54 (s, 2H), 2.41 (m, 8H). MS [M+H]$^+$: 334.4.

Test Example 1

Analgesic Effect of the Compounds of the Present Invention

1. Experimental purposes: To determine the analgesic activity of Compound (4) hydrochloride and Compounds (1), (2), (3), (5) in a mouse acetic acid writhing model.

2. Experimental materials: Kunming mice (18-22 g), half male and half female, were provided by the Experimental Animal Center of the Academy of Military Medical Sciences.

3. Experimental methods and results:

The mice were weighed and labeled, 10 mice in each group (half male and half female), the mice were divided into 7 groups, including 5 experimental groups (using Compound (4) hydrochloride, Compound (1), (2), (3), (5), respectively), positive control group (using NMED-160) and negative control group (using normal saline). Among them, NMED-160 used in the positive control group was a selective small molecule N-type calcium ion channel blocker, which had entered the phase II clinical trial and could be synthesized by referring to document[11], and the structural formula thereof is as follows:

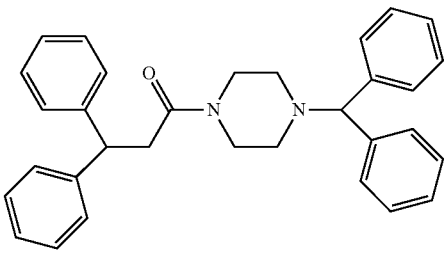

NMED-160

The mice were intragastrically administered with drug (30 mg/kg). After 40 minutes, 0.4 mL of 0.6% (v/v) acetic acid was intraperitoneally injected. After 5 minutes, the number of mouse writhings in the subsequent 15 minutes was recorded. The inhibition rate of the drug on the acetic acid writhing in mice was calculated according to the following formula, and the analgesic effect of the drug was evaluated. The results are shown in Table 2.

wherein:

$$\text{Writhing\_Inhibition\_Rate } (\%) = \frac{A-B}{A} \times 100\%$$

A represents the number of writhings in the negative control group;

B represents the number of writhings in the experimental groups or the positive control group.

TABLE 2

| | Analgesic results | |
|---|---|---|
| Drug | Writhing inhibition rate (%) | Number of animals per group (mouse) |
| NMED-160 | 51.75 | 10 |
| Compound (1) | 58.77 | 10 |
| Compound (2) | 54.66 | 10 |
| Compound (3) | 23.17 | 10 |
| Compound (4) hydrochloride | 39.68 | 10 |
| Compound (5) | 46.87 | 10 |

Table 2 shows that the compound and the pharmaceutically acceptable salt thereof according to the present invention have significant analgesic effects; wherein the analgesic effects of Compounds (1) and (2) are comparable to that of NMED-160.

Test Example 2

N-Type Calcium Ion Channel Current Suppressing Activity of the Compound of the Present Invention 1. Experimental Purpose:
To determine the current suppressing effects of Compound (4) hydrochloride and Compounds (1), (2), (3), (5) of the present invention on N-type calcium ion channel ($\alpha_{1B}/\beta_{1b}/\alpha2_\delta$) transiently expressed in Xenopus oocytes.

2. Experimental Materials:
Xenopus oocytes.
N-type calcium ion channel cDNAs plasmid $\alpha_{1B}$ (GenBank accession no. AF055477)/$\alpha_{2\delta}$ (AF286488)/$\beta_{1b}$ (L06110), rabbit $\alpha_{1C}$ (X15539), human $\alpha_{1A}$ (NM000068), rat $\alpha_{1E}$ (NM 009782) and rat HERG (U04270).

3. Experimental Method:
(1) Amplification of Different Subunit cDNAs of Calcium Channel:
E. coli competent cells containing $\alpha_{1B}$, $\alpha_2\delta$, $\beta_{1b}$ plasmids (cDNAs plasmids) were separately placed in LB solution (100 mL) containing ampicillin (50 μg/mL), and shaken at 37° C., 200 rpm for 12 to 17 hours, for next day use.

(2) Extraction of Plasmids:
4 mL of the above culture of E. coli was centrifuged for 5 minutes in a tabletop centrifuge (12000 g), the supernatant was discarded, and the tube was placed upside down on a paper towel to absorb the remaining culture solution. 250 μL of cell suspension solution was added to the above tube, vortexed or blown to fully suspend the cells, and the suspended cells were transferred to a 5 mL sterilized centrifuge tube. 250 μL of cell lysis solution was added thereto and the tube was inverted 4 times to mix well. The incubation time was approximately 1 to 5 minutes. Additionally, 10 μL of alkaline protease solution was added thereto and the tube was inverted 4 times to mix well, and incubation was performed for 5 minutes at room temperature. The alkaline protease was capable of inactivating nucleases and other proteins released during cell lysis that affected the quality of the isolated plasmids. Then, 350 μL of neutralizing solution was added to the centrifuge tube and the tube was rapidly inverted 4 times to mix well, and the centrifuge tube was subjected to centrifugation at the maximum speed (14,000 g) for 10 minutes at room temperature.

About 850 μL of the clear lysate from the above centrifugation was transferred to the prepared spin-column without agitating or transferring any white precipitate along with the supernatant. Centrifugation was performed at room temperature for 1 minute at the maximum speed with centrifuge, the centrifuge tube was taken from the collection tube, the liquid in the collection tube was discarded, and the spin-column was reinserted into the collection tube. 750 μL of the column washing solution previously diluted with 95% (w/w) ethanol was added thereto. Centrifugation was performed at room temperature for 1 minute at the maximum speed with centrifuge, the centrifuge tube was taken from the collection tube, the liquid in the collection tube was discarded, and the spin-column was reinserted into the collection tube. 250 μL column washing solution was added, and the washing was repeated once. Centrifugation was performed at room temperature for 2 minutes at the maximum speed with centrifuge.

The spin-column was transferred to a sterilized 1.5 mL centrifuge tube, which must be handled carefully without transferring the washing solution along with the spin-column. 100 μL of nuclease-free water was added to elute plasmid DNA (optionally waited for 2 minutes for complete dissolution), and centrifugation was performed at the maximum speed for 1 minute at room temperature with centrifuge. After elution, the spin-column was taken out and discarded. The centrifugal liquids were combined and stored at −20° C. for later use and the concentration was measured.

(3) Isolation and Culture of Xenopus oocytes:
Surgical instruments were immersed in 75% (w/w) ethanol for 30 minutes and taken out to dry. Number 5 thread was sterilized in boiling water for 10 minutes.
Xenopus laevis was buried in crushed ice for about 40 minutes for anesthetization. The anesthetized Xenopus laevis was taken out and placed on the tiled crushed ice in an abdomen up position, and its head and limbs were buried with crushed ice. Its lower abdomen skin was sterilized with alcohol cotton ball, then picked up (at left or right side of the middle) with a needle, and cut with a pair of ophthalmic scissors to form a small opening of about 1 cm. The muscle layer was cut in the same way (carefully not to damage any internal organs, and oocytes could be seen after cutting the muscle layer). Lobules with a size of 1 cm³ were taken out with tweezers and scissors, and placed in a pre-prepared culture dish containing OR-2 (containing penicillin), and the muscle layer and the skin layer were sutured, respectively.

The oocytes were transferred into a sterilized glass tube and washed repeatedly with OR-2 solution until the residual blood was washed away. Collagenase solution was added thereto and shaken for about 1 hour, and then fresh collagenase solution was replaced and the shaking was continued for about 1 hour (most of the isolated or single cells could be seen at this time).

After removing the digestive solution, the cells were washed 5-6 times with OR-2 solution, transferred to a culture dish containing ND-96 solution to select phase V mature cells and place them into ND-96 solution, and stored in a biochemical incubator for use at 1° C., and the solution was replaced once per day.

(4) Injection of Calcium Channel Plasmid:
Plasmids $\alpha_{1B}$, $\alpha_2\delta$, $\beta_{1b}$ were injected into Xenopus oocytes in concentration ratio of 1:1:1, and the total volume of the three plasmids injected into per cell was about 46 nL. The injected cells were placed in ND-96 medium at 18° C. for 48 hours, then the expressed current was recorded.

(5) Current Record:
Perfusion administration method was adopted with a flow rate of 3 mL/min and a test drug concentration of 10 μM. Using two-electrode voltage clamp technique, the cell was clamped at −100 mV, stepped at 10 mV, depolarized to +60 mV, and the current was recorded.

The experimental results of the N-type calcium ion channel current suppression experiment are shown in Table 3.

Current inhibition rate (%)=100×(current amplitude after administration−current amplitude before administration)/current amplitude before administration

TABLE 3

Experimental results of compounds inhibiting N-type calcium ion channel currents (10 μM)

| Drug | Current inhibition rate (%) | Cell number |
| --- | --- | --- |
| Compound (1) | 70.6 | 3 |
| Compound (2) | 65.6 | 3 |
| Compound (3) | 42.3 | 3 |
| Compound (4) hydrochloride | 54.1 | 3 |
| Compound (5) | 45.3 | 3 |

The above results indicate that the compounds and the pharmaceutically acceptable salt thereof according to the present invention have strong inhibitory effects on N-type calcium ion channel.

Test Example 3

Current-Inhibition Activity of the Compounds of the Present Invention in P/Q-Type Calcium Channel, Herg Channel, Sodium Channel, and Potassium Channel (1) Enzyme Digestion Linearization of P/Q-Type and Herg Channel DNAs 1. The subunits of P/Q-type calcium channel ($\alpha_{2\delta}$, $\beta_{1b}$, $\alpha_{1B}$, $\alpha_{1E}$, $\alpha_{1A}$, $\alpha_{1C}$) and Herg channel DNA were from the same source as in. Test Example 2, and the enzyme digestion was carried out according to the following system:

| | |
|---|---|
| Hpa I | 1 µL |
| 10 × MBuffer | 2 µL |
| DNA($\alpha_{2\delta}$) | ≤1 µg |
| Sterile water | added to total volume of 20 µL; |
| Xba I | 1 µL |
| 10 × M Buffer | 2 µL |
| DNA($\beta_{1b}$) | ≤1 µg |
| Sterile water | added to total volume of 20 µL; |
| Not I | 1 µL |
| 10 × M Buffer | 2 µL |
| DNA($\alpha_{1B}$) | ≤1 µg |
| Sterile water | added to total volume of 20 µL; |
| Xba I | 1 µL |
| 10 × M Buffer | 2 µL |
| DNA($\alpha_{1E}$) | ≤1 µg |
| Sterile water | added to total volume of 20 µL; |
| Xba I | 1 µL |
| 10 × M Buffer | 2 µL |
| DNA($\alpha_{1A}$) | ≤1 µg |
| Sterile water | added to total volume of 20 µL; |
| Xba I | 1 µL |
| 1 × M Buffer | 2 µL |
| DNA($\alpha_{1C}$) | ≤1 µg |
| Sterile water | added to total volume of 20 µL; |
| Xba I | 1 µL |
| 10 × M Buffer | 2 µL |
| DNA(Herg) | ≤1 µg |
| Sterile water | added to total volume of 20 µL; | the plasmid DNAs were subjected to enzyme digestion according to the above reaction systems, and incubated at 37° C. for 1 hour.

2. DNA Purification and RNA Enzymes Removal:

a. To the plasmid DNA sample that had been enzyme digested, 0.1 times volume of 10× proteinase K buffer, 0.1 times volume of 5% SDS solution, 20 mg/mL proteinase K (final concentration was 100 µg/mL) were added, and incubation reaction was performed at 37° C. for 1 hour;

b. The above reaction mixture was transferred to a clean 1.5 mL eppendorf tube, added with an equal volume of Tris-balanced phenol:chloroform:isoamyl alcohol (25:24:1), shaken for 1 minute, centrifuged at 12000 rpm for 2 minutes at room temperature (20-25° C.) (if the organic and inorganic phases were not sufficiently separated, centrifugation was repeated for an extended period of time);

c. The upper aqueous phase was carefully transferred to another clean 1.5 mL eppendorf tube, the interfacial layer between the two phases and the organic phase were discarded;

d. An equal volume of chloroform:isoamyl alcohol (24:1) was added thereto, and centrifuged at 12000 rpm for 2 minutes at room temperature (20-25° C.);

e. The upper aqueous phase was carefully transferred to another clean 1.5 mL eppendorf tube, added with 0.1 times volume of 3M sodium acetate (pH 5.2) and 2.5 times volume of 95% (W/W) ethanol, shaken to mix well, and stood at −20° C. overnight (12-16 hours);

f. Centrifugation was performed at 12000 rpm for 40 minutes at a low temperature (<4° C.);

g. The supernatant was carefully removed without agitating the sediment, and all droplets attached to the tube wall were sucked out with a sucker;

h. To the sediment obtained by the previous step, half-tube of 70% (w/w) ethanol was added, shaken to mix well, and centrifuged at 12000 rpm for 2 minutes at low temperature (<4° C.);

i. The supernatant was carefully removed, and the previous step was repeated;

j. The 1.5 mL eppendorf tube was kept in open state at room temperature (20-25° C.) until the residual liquid was evaporated;

k. An appropriate volume of Nuclease-free water was added thereto with rinsing the tube wall thoroughly, mixed well to completely dissolve the template DNA, measured to determine the concentration value, and stored at −20° C. for later use.

3. In Vitro Transcription of Calcium Ion Channel Subunits and HERG Channel cDNA into cRNA[13,14]:

The reactants were added in the following order of the reaction systems:

Linearized templates of $\alpha_{1A}$, $\beta_{1b}$, $\alpha_{2\delta}$, $\alpha_{1E}$, $\alpha_{1A}$, $\alpha_{1C}$ subunit and Herg channel subunit;

T7 Transcription 5×Buffer 20 µL;

rNTPs (25 mM ATP, CTP, UT, each 7.5 µL+3 mM GTP, 0.6 µL+nuclease-free water, 6.9 µL);

Linear DNA templates (5-10 µg in total)+nuclease-free water 32.5 µL;

Ribom7 hat analog, 40 mM, 7.5 µL;

MixE, 10 µL.

a. The reaction mixture was taken out from the incubator, added with RQ1 Rnase-Free Dnase (in a ratio of 1 u enzyme per µg template DNA), and the incubation reaction was performed at 37° C. for 15 minutes;

b. An equal volume of water-balanced phenol:chloroform:isoamyl alcohol (25:24:1) was added thereto, shaken for 1 minute, and centrifuged at 12,000 rpm for 2 minutes at room temperature (20-25° C.) (if the organic and inorganic phases were not fully separated, the centrifugation was repeated for an extended period of time);

c. The upper aqueous phase was carefully transferred to another clean 1.5 mL eppendorf tube, added with an equal volume of chloroform:isoamyl alcohol (24:1), and centrifuged at 12000 rpm for 2 minutes at room temperature (20-25° C.);

d. The supernatant was carefully transferred to another clean 1.5 mL eppendorf tube, added with 0.1 times volume of 3M sodium acetate (pH 5.2) and 2.5 times volume of 95% (w/w) ethanol, shaken to mix well, and stood at −20° C. overnight (12-16 hours);

e. Centrifugation was performed at 12,000 rpm for 40 minutes at low temperature (<4° C.);

f. The supernatant was carefully removed without agitating the sediment, and all droplets attached to the tube wall were sucked out with a sucker;

g. To the sediment obtained in the previous step, half-tube of 70% (w/w) ethanol was added;

h. The supernatant was carefully removed, and the previous step was repeated;

i. The 1.5 mL eppendorf tube was kept in open state at room temperature (20-25° C.) until the residual liquid was evaporated, an appropriate volume of nuclease-free water was added with rinsing the tube wall thoroughly, mixed well to completely dissolve mRNA, and stored at −70° C. for later use.

4. Injection of *Xenopus* oocytes:

After drawing the special injection needle with two-step electrode drawing instrument, the needle was used to puncture a clean thin tissue paper in order to enlarge the tip diameter of the needle, and polished with polishing instrument to make the needle tip smooth and flat. The diameter of the needle tip was preferably 6-10 μm. Prior to installing the injection needle, Light mineral oil was injected into the needle to lubricate the tube wall. Based on the concentrations of the original subunit cRNAs, the injection concentrations were adjusted to approximately 2 ng/nL and separately mixed (1:1:1). 1 μL of the mixed cRNA was carefully dropped onto a clean parafilm, and the cRNA was indrawn into the injection needle by using a microinjector (Note: the contamination of RNase should be prevented; the indrawing of air into the injection needle should be prevented; both of which could affect the expression of cRNA in the oocytes). The selected healthy mature oocytes of phases V and VI were placed in a Petri dish with a mesh (which prevented the cells from sliding in the dish) at the bottom. The 3D micromanipulator was carefully adjusted so that the needle tip touched cell surface. If the cell was in good condition, a resistance would be felt when the needle tip touched the cell, and wrinkles formed by the tension on the cell membrane would be seen. The needle tip should not puncture the cell too deeply, and it was advisable to just pass the needle tip through the cell membrane. 46.5 nl of cRNA was injected into the oocyte, and the cell swelled slightly after the injection. After waiting for 30 s, the injection needle was pulled out and observed if any cell contents spilled, and if so, discarded the cell. In addition, if the needle tip was easily pierced into the cell without breakthrough feeling, it indicated that the cell was tension-free and in poor condition, meaning that the cell might not be able to clamp to the desired potential, and the cell should be discarded as well. The injected oocytes were placed in ND-96 solution and incubated for 48 hours in a biochemical incubator (18° C.) (ND-96 solution was replaced everyday), and the expressions of P/Q-type calcium ion channel current and Herg channel current were recorded separately.

5. Recording Extracellular Fluid and Intracellular Fluid of Calcium Channel Expressed by *Xenopus*:

Extracellular fluid (mM): $BaCl_2$ 5, N-methyl-D-glucamine 50, KCl 5, HEPES 5, adjusted to pH 7.4 with methanesulfonic acid.

The intracellular fluid was 3 mM KCl. Preparation of BAPTA: BAPTA was dissolved in 10 mM Hepes and the pH was adjusted to 7.2 with CsOH.

(2) Primary Cultured Hippocampal Neurons

1. Culture of Hippocampal Neurons:

Newborn Wistar rats were taken and sterilized with 75% (w/w) ethanol. The brain was taken under aseptic condition, and the hippocampus was peeled off and placed in an anatomical solution in an ice bath. The hippocampus was cut into tissue blocks of 1-2 mm³, digested with an anatomical solution containing 0.25% trypsin for 30 minutes at 37° C., and then the digested tissue blocks were transferred to a planting solution to terminate digestion, and a pipette with an appropriate caliber (having tip diameter of 2 mm) was used to blow and beat the cells in the planting solution so that the cells were evenly dispersed to prepare a cell suspension, and a small amount of the suspension was taken to count the cells in a trypan blue dye. An appropriate amount of planting solution was added, the cells were inoculated in a 35 mm culture dish previously coated with polylysine at a density of $1\times10^5$/mL, and placed in a 10% carbon dioxide incubator at 36° C. overnight, the culture medium was replaced after 24 hours, and the planting solution was changed to 2 mL of culture solution. Hereafter, the culture solution was changed once every three days at half volume, and the cultured cells during the period of 12-15 days were used for patch clamp experiments. In order to inhibit non-neuronal hyperproliferation, an appropriate amount of cytarabine was added into the medium on the third day of culture (6 μL of cytarabine stock solution was added to each dish to reach a final concentration of 3 μg/mL).

2. Recording Intra-Electrode Fluid and Extracellular Fluid of Hippocampal Neuron Current:

The recording fluids used for whole-cell recording were mainly intra-electrode fluid and extracellular fluid.

Recording intra-electrode fluid components (mM): KCl 140, HEPES 10, EGTA 10, and the pH was adjusted to 7.2-7.4.

Components of extracellular fluid (mM): NaCl 140, KCl 5, $MgCl_2$ 1, HEPES 10, Glucose 10, $CaCl_2$ 3, and the pH was adjusted to 7.2-7.4 with NaOH. If the experiment required blocking sodium current, 1 μM tetrodotoxin (TTX) could be added to the extracellular fluid. If the experiment required blocking potassium current and only CsCl could not completely block potassium current, tetraethylammonium (TEA) or 4-aminopyridine (4-AP) could be added to the intra-electrode fluid and the extracellular fluid.

The measurement results are shown in Table 4.

TABLE 4

Current inhibition results for P/Q-type calcium channel, Herg channel, sodium channel and potassium channel

| Drug (10 μM) | P/Q-type calcium channel | Herg channel | TTX sensitive sodium channel | Voltage-gated potassium channel |
|---|---|---|---|---|
| Compound (1) | — | — | — | — |
| Compound (2) | — | — | — | — |
| Compound (3) | — | — | — | — |
| Compound (4) hydrochloride | — | — | — | — |
| Compound (5) | — | — | — | — |

"—" indicates that the compound had no effect on this channel current.

The experimental results show that the compound and pharmaceutically acceptable salt thereof according to the present invention have no blocking or inhibiting effect on P/Q-type calcium channel, Herg channel, TTX-sensitive sodium channel and voltage-gated potassium channel.

Therefore, the compounds and pharmaceutically acceptable salt thereof according to the present invention, are capable of specifically inhibiting an N-type calcium ion channel.

Test Example 4

Rapid Evaluation of Pharmacokinetics in Rats

1. Materials and Instruments:

Compound (1) was dissolved in 25% (w/v) aqueous solution of hydroxypropyl-β-cyclodextrin;

Megestrol: internal standard substance, purchased from the Inspection Institute of China;

Hydroxypropyl-β-cyclodextrin: purchased from Xi'an Deli Biochemical Co., Ltd., prepared as a 25% (w/v) aqueous solution of hydroxypropyl-β-cyclodextrin;

Acetonitrile, methanol: chromatographically pure, purchased from Fisher Company;

Pure water;

Adult SD rats, 180-220 g in body weight, male, purchased from the Animal Center of the Academy of Military Medical Sciences, Animal Certificate SCXK-(Army)-2012-0004;

Liquid chromatography-mass spectrometer (LC-MS/MS), triple quadrupole cascade LC-MS/MS (API 5000);

LDZ5-2 type centrifuge (Beijing Medical Centrifuge Factory);

MicroCL21R high speed refrigeration centrifuge (Thermo Company, USA);

JJ-1 type precision booster electric mixer (Changzhou Guohua Electric Co., Ltd.);

XW-80A type vortex mixer (Shanghai Qingpu Huxishi Instrument Factory);

Sartorius BS110S Electronic Analytical Balance (Beijing Sartorius Balance Co., Ltd.), Libror EB-330D Electronic Analytical Balance (Shimadzu, Japan).

2. Drawing Standard Curve:

1 mg/mL mother solution of Compound (1) was prepared with acetonitrile, and gradually diluted to obtain standard solutions with a series of concentrations; multiple portions of blank rat plasma were taken at 0.05 mL, separately added with 0.005 mL standard solutions of the series of concentrations and 0.3 mL of acetonitrile containing internal-standard substance megestrol (10 ng/mL), resulting in that, the final concentrations of Compound (1) were 1 ng/mL, 2 ng/mL, 5 ng/mL, 20 ng/mL, 100 ng/mL, 200 ng/mL, 500 ng/mL, 1000 ng/mL, 2000 ng/mL, respectively, then vortexed for 1 minute on a vortex mixer, centrifuged for 10 minutes (14000 g), about 0.15 mL of the supernatant was taken and placed in an injection vial, and injected 5 μL into LC-MS/MS for analysis.

Quality control sample: The mother solution of Compound (1) (1 mg/mL) was diluted stepwise into three standard solutions of low, medium and high concentrations. A plurality of blank rat plasma were taken at 0.05 mL, separately added with 0.005 mL standard solutions of low, medium and high concentrations and 0.3 mL of acetonitrile containing internal-standard substance megestrol (10 ng/mL), resulting in that the final concentrations of Compound (1) were 2 ng/mL, 50 ng/mL, 1600 ng/mL, respectively, which were used as quality control samples of Compound (1) (repeated 3 samples for each concentration, n=3), vortexed for 1 minute on vortex mixer, centrifuged for 10 minutes (14000 g), about 0.15 mL of the supernatant was taken and placed in injection vial, and injected 5 μL into LC-MS/MS for analysis.

Operation Conditions of Liquid Chromatography:

Column: Kromasil 100-5 C18, Dim 50×2.1 mm, (Sweden);

Mobile phase composition: mobile phase A was water (containing 0.1% formic acid), mobile phase B was acetonitrile (containing 10 mM ammonium acetate and 0.1% formic acid), and the gradient elution procedure was shown in Table 5.

TABLE 5

Mobile phase gradient elution procedure

| Time (min) | Flow rate (mL/min) | Mobile phase A (%) | Mobile phase B (%) |
|---|---|---|---|
| 0.5 | 0.6 | 90 | 10 |
| 2 | 0.6 | 5 | 95 |
| 2.5 | 0.6 | 5 | 95 |
| 2.6 | 0.6 | 90 | 10 |
| 4 | 0.6 | 90 | 10 |

MS/MS Quantitative Analysis Conditions:

The ionization mode was electrospray (ESI) condition, positive ion detection;

The detected m/z values of Compound (1) and the internal standard substance were 427.168 and 385.2, respectively. Selective ion (SRM) method was used for detection: the fragment ion of the m/z 427.168 was m/z 250.1, and CE was 18; and the fragment ion of the internal standard substance m/z 385.2 was m/z 267.3, and CE was 25.

A standard curve was drawn for the measured peak areas relative to the concentrations of Compound (1), the linear range was 1 ng/mL to 2000 ng/mL, the lowest detection line was 1 ng/mL, and the linearity was good. The precision of the detected concentrations of the quality control samples and the accuracy between them and the true concentrations were all within ±15%, indicating that the detection method was accurate and reliable.

3. Rapid Evaluation of PK in Rats:

Six adult SD rats were randomly numbered, and divided into 2 groups to receive intravenous injection (i.v., 1.85 mg/kg) and oral administration (p.o., 11 mg/kg) of Compound (1), respectively; blood samples were collected at 0.1 mL before administration and 2 minutes, 5 minutes, 15 minutes, 30 minutes, 60 minutes, 2 hours, 4 hours, 7 hours and 24 hours after administration, placed in anticoagulation tubes, centrifuged for 15 minutes (3500 rpm) to separate plasma, and 0.05 mL plasma samples were accurately taken and frozen in a refrigerator at −30° C. for later tests.

Figure 2:
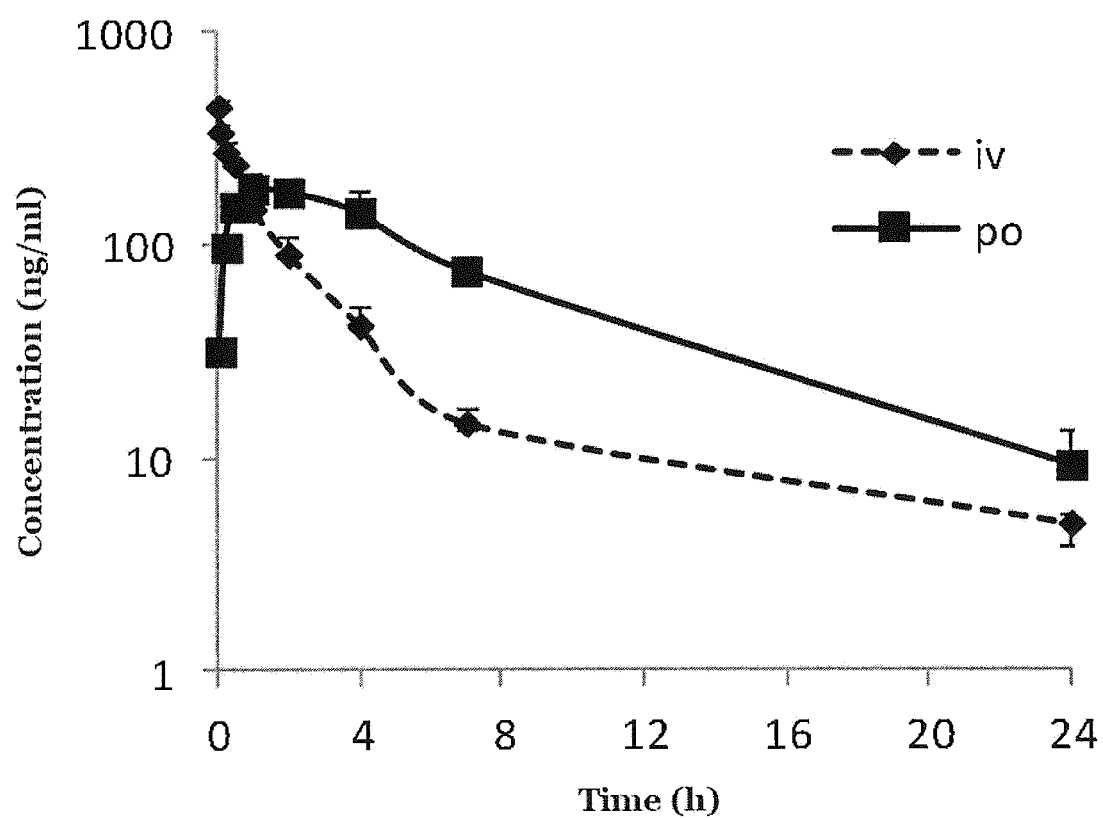
FIG. 2 shows the concentrations of Compound (1) in rats' plasmas after intravenous administration and oral administration in Test Example 4 of the present invention.

To the 0.05 mL rat plasma sample, 0.3 mL of acetonitrile containing the internal standard substance megestrol (100 ng/mL) and 0.005 mL of blank acetonitrile were added, vortexed for 1 minute on a vortex mixer, and centrifuged for 10 minutes (14,000 g), about 0.15 mL of the supernatant was taken and placed into an injection vial, injected 5 μL to LC-MS/MS for detection and analysis by referring to the method of the above section 2. In combination with the standard curve obtained in the above section 2, the concentrations of Compound (1) in 6 rats at different time points were calculated, as shown in FIG. 1, in which, 1 # to 3 # were of i.v. administration, and 4 # to 6 # were of p.o. administration. The results of 1 # to 3 # were averaged, the results of 4 # to 6 # were averaged, and the relationship curves of the average concentrations of Compound (1) in the rats of i.v. administration and in the rats of p.o. administration against time were obtained and shown in FIG. 2. The Winnolin pharmacokinetic software was used to analyze the measured data and calculate the main pharmacokinetic parameters, including the area under curve (AUC), clearance rate (CL), apparent distribution volume (V), terminal elimination half life ($t_{1/2}$) and mean residence time (MRT) for the intravenous injection, as well as the area under curve (AUC), terminal elimination half life ($t_{1/2}$), mean residence time (MRT), peak concentration ($C_{max}$), time to peak ($T_{max}$) and biological force (F) for the oral administration. The obtained pharmacokinetic parameters are shown in Table 6.

TABLE 6

Pharmacokinetic parameters after intravenous injection (1.85 mg/kg) and oral administration (11 mg/kg) of Compound (1) in rats (n = 3)

| Parameter | Unit | Compound (1) | |
| --- | --- | --- | --- |
| | | Intravenous injection (1.85 mg/kg) | Oral administration (11 mg/kg) |
| AUC | μg/L*h | 750.1 ± 98.2 | 1674.4 ± 222.4 |
| MRT | h | 3.87 ± 0.18 | 5.6 ± 0.46 |
| $t_{1/2}$ | h | 5.0 ± 0.88 | 5.4 ± 1.5 |
| $C_{max}$ | ng/mL | — | 187.7 ± 28.5 |
| $T_{max}$ | h | — | 1.33 ± 0.58 |
| CL | L/h/kg | 2.38 ± 0.29 | — |
| V | L/kg | 12.39 ± 3.17 | — |
| F | % | — | 44.7 ± 5.93 |

The results of pharmacokinetic study in rats showed that the in vivo average clearance rate of Compound (1) after intravenous administration was 2.38 L/h/kg, which was slightly lower than rat liver blood flow (3.3 L/h/kg)[15], suggesting that Liver metabolism had about 70% effect on the clearance of compound (1) in vivo; the stable apparent distribution volume V was 12.39 L/kg, which was much larger than the volume of rat plasma (0.03 L/kg)[15] and the total water volume in rat (0.6 L/kg)[15], suggesting that most of the compound was mainly distributed in extravascular tissues, and the probability of exposure in target tissues was also large; the average time to peak after oral administration was 1-2 h, suggesting that the intestinal absorption of the compound was good; as compared with the in vivo drug exposure amount after oral administration, the average bioavailability was 44.7%, the metabolic properties were good. In summary, the compound as an analgesic drug has good pharmacokinetic properties in rats, and further researches including the drug distribution in target sites of brain tissue under steady state conditions can be carried out.

Test Example 5

Evaluation of the Central Nervous System Distribution

1. Materials and Instruments:
Identical to those of Test Example 4.
2. Drawing Standard Curves:
This was carried out by referring to the method of section 2 in Test Example 4;
In addition, the blank rat plasma was replaced with blank rat brain homogenate, and a standard curve of Compound (1) for rat brain homogenate was drawn.
3. Evaluation of Central Nervous System Distribution of Compound (1) in Plasma and Brain Homogenate of Rats:
Compound (1) was prepared at a concentration of 4 mg/mL with a 25% (w/v) aqueous solution of hydroxypropyl-β cyclodextrin. Three adult SD rats were randomly numbered, first injected intravenously with 0.4 mL Compound (1) solution, and then slowly instilled with the Compound (1) solution (0.4 mL/h) for 2 hours, respectively. Blood samples in volume of 0.1 mL were collected before the administration and 30 minutes, 60 minutes and 2 hours after the administration, respectively, and placed in anticoagulant tubes, centrifuged for 15 minutes (3500 rpm) to separate plasma, and 0.05 mL plasma samples were accurately taken, and frozen in a refrigerator at −30° C. for later test.
After 2 hours of blood collection, the rats were executed by femoral artery bleeding, and the whole brain and spinal cord were taken, rinsed with physiological saline, placed on filter paper to suck water, and frozen in a refrigerator at −30° C. for later test.

To the 0.05 mL of rat plasma sample, 0.3 mL of acetonitrile containing the internal standard substance megestrol (100 ng/mL) and 0.005 mL of blank acetonitrile were added, vortexed for 1 minute on a vortex mixer, and centrifuged for 10 minutes (14,000 g). About 0.15 mL of the supernatant was taken and placed in an injection vial, injected 5 μL to LC-MS/MS for detection and analysis by referring to the method of Test Example 4. In combination with the standard curve obtained in the above section 2, the concentrations of Compound (1) in the rat plasma samples were calculated.

The rat brain tissue samples and the rat spinal cord samples were weighed and added to normal saline at 1:4 (v/v) to prepare a homogenate. 0.05 mL of the homogenate was taken, added with 0.3 mL of acetonitrile containing the internal standard substance megestrol (100 ng/mL) and 0.005 mL of blank acetonitrile, fully vortexed for 1 minute on a vortex mixer, and centrifuged for 10 minutes (14000 g); about 0.15 mL of the supernatant was taken and placed into an injection vial, injected 5 μL to LC-MS/MS for detection and analysis by referring to the method of Test Example 4. In combination with the standard curve obtained in above section 2, the concentrations of Compound (1) in rat brain tissue and spinal cord samples were calculated.

TABLE 7

Concentrations of Compound (1) in rat plasma, rat brain tissue, rat spinal cord after administration for 2 hours (n = 3).

| Concentration | | | $K_p$ | |
| --- | --- | --- | --- | --- |
| Rat plasma | Rat brain | Rat spinal | | |
| (ng/mL) | tissue (ng/g) | cord (ng/g) | $K_{p(b/p)}$ | $K_{p(s/p)}$ |
| 270.7 ± 47.4 | 808.3 ± 233.8 | 998.3 ± 393.5 | 3.0 ± 0.71 | 3.7 ± 1.3 |

The results as shown in Table 3 indicated that after exposure in plasma, Compound (1) easily entered the brain tissue and the spinal cord through blood-brain barrier, and its contents in the brain tissue and in the spinal cord were 3-4 times of the content in plasma; when the compound was used as an analgesic drug of central target, this distribution characteristic was beneficial to its efficacy.

It is apparent that the above-described examples are merely provided for illustrative purpose, and are not intended to limit embodiments. For those skilled in the art, other variations or modifications in various forms may be made in light of the above description. There is no need and no way to exhaust all of the embodiments. That is, obvious changes or variations resulting therefrom are still within the scope of the invention.

REFERENCE DOCUMENTS

[1] Newton P M, Messing R O. Channels, 2009, 3(2): 77-81.
[2] Tomoyuki KONDA, Azusa ENOMOTO, Akira TAKAHARA, and hiroshi YAMAMOTO, Effects of LN-Type Calcium Channel Antagonist, Cilnidipine on Progressive Renal Injuries in Dahl Salt-Sensitive Rats. Biol. Pharm. Bull. 2006, 29(5) :933-937.
[3] Tomoyuki Konda, Azusa Enomoto, et al. The N- and L-Type Calcium Channel Blocker Cilnidipine Suppresses Renal Injury in Dahl Rats Fed a high-Sucrose Diet. an Experimental Model of Metabolic Syndrome Nephron Physiol, 2005, 101:1-13.

[4] Ishikawa T, Nobukata h, et al. Effects of $Ca^{2+}$ channel blocker cilnidipine in comparison with that of amLodipine and nifedipine on insulin resistance in Dahl S rats. Jpn Pharmacol Ther. 1999, 27, 53-60.

[5] Yamamoto T, Takahara A. Current Topics in Med Chem., 2009, 9: 377-395.

[6] Teodori. J Med Chem, 2004, 47: 6070-6081.

[7] Knutsen. Bioorg Med Chem Lett, 2007, 17(3): 662-667.

[8] Yamamoto. Bioorg Med Chem, 2006, 14: 5333-5339.

[9] Yamamoto. Bioorg Med Chem Lett, 2008, 18(17): 4813-4816.

[10] Tyagarajan. Bioorg Med Chem Lett, 2011, 21(17): 869-873.

[11] Zamponi G W, et al. Bioorg Med Chem Lett, 2009, 19: 6467-6472.

[12] Pajouheshh, et al. Bioorg Med Chem Lett, 2010, 20: 1378-1383.

[13] Hou Yunde. Guide to Molecular Cloning Experiments (2$^{nd}$ Edition), Science Press, 2002.

[14] Lai Maode. Medical Molecular Biology, People's Medical Publishing House, 1999.

[15] Davis B, Morris T. Pharma Res, 1993, 10, 1093-1095.

What is claimed is:

1. A compound of Formula I or a pharmaceutically acceptable salt thereof:

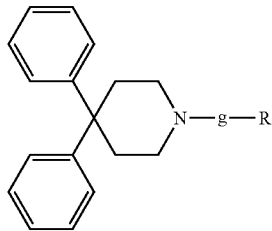

I wherein:

g is selected from the group consisting of methylene, carbonyl, methyleneacyl, ethylideneacyl, 1,3-propylideneacyl, 1,2-propylideneacyl, 1,4-butylideneacyl, 1,3-butylideneacyl and 1,2-butylideneacyl;

R is selected from the group consisting of substituted phenyl, thienyl and benzoxazolinonyl;

the substituted phenyl is substituted with one or more substituents, the substituent is selected from the group consisting of methoxy and dimethylamino.

2. The compound of Formula I or a pharmaceutically acceptable salt thereof according to claim 1, which is selected from the group consisting of the following compounds and pharmaceutically acceptable salts thereof:

6-(3-(4,4-diphenylpiperidinyl)-propionyl)benzoxazolin-2-one;

6-(3-(4,4-diphenylpiperidinyl)-acetyl)benzoxazolin-2-one;

1-(4-dimethylaminobenzyl)-4,4-diphenylpiperidine;

1-(3,4,5-trimethoxybenzyl)-4,4-diphenylpiperidine;

1-(2-methylthienyl)-4,4-diphenylpiperidine.

3. A pharmaceutical composition, comprising the compound or a pharmaceutically acceptable salt thereof according to claim 1.

4. A method of blocking or inhibiting a N-type calcium ion channel in vivo or in vitro, comprising the step of: administering to a subject in need thereof an effective amount of the compound or a pharmaceutically acceptable salt thereof according to claim 1.

5. A method for treatment of a pain, a stroke, a cerebral ischemia, an alcohol addiction, an alcoholism, a renal disease, an addictive disorder caused by an analgesic drug or a tolerable disorder caused by an analgesic drug, comprising the step of: administering to a subject in need thereof an effective amount of the compound or a pharmaceutically acceptable salt thereof according to claim 1.

6. The pharmaceutical composition according to claim 3, further comprising a pharmaceutically acceptable excipient.

7. A method of blocking or inhibiting a N-type calcium ion channel in vivo or in vitro, comprising the step of: administering to a subject in need thereof an effective amount of the pharmaceutical composition according to claim 3.

8. A method for treatment of a pain, a stroke, a cerebral ischemia, an alcohol addiction, an alcoholism, a renal disease, an addictive disorder caused by an analgesic drug or a tolerable disorder caused by an analgesic drug, comprising the step of: administering to a subject in need thereof an effective amount of the pharmaceutical composition according to claim 3.

9. The method according to claim 5, wherein, the pain is a postoperative pain, a migraine, a visceral pain or a neuropathic pain.

10. The method according to claim 5, wherein, the renal disease is an acute renal failure, a chronic renal failure or a renal insufficiency.

11. The method according to claim 8, wherein, the pain is a postoperative pain, a migraine, a visceral pain or a neuropathic pain.

12. The method according to claim 8, wherein, the renal disease is an acute renal failure, a chronic renal failure or a renal insufficiency.

* * * * *